(12) United States Patent
Arigoni et al.

(10) Patent No.: US 7,700,315 B2
(45) Date of Patent: Apr. 20, 2010

(54) SERPIN IN BIFIDOBACTERIA

(75) Inventors: Fabrizio Arigoni, Geneva (CH);
Stéphanie Blum, Lausanne (CH);
Michèle Delley, Vauderens (CH); Mark Alan Schell, Athens, GA (US); Eduardo Schiffrin, Crissier (CH)

(73) Assignee: Nestec S.A., Vevey (CH)

( * ) Notice: Subject to any disclaimer, the term of this patent is extended or adjusted under 35 U.S.C. 154(b) by 453 days.

(21) Appl. No.: 10/470,559

(22) PCT Filed: Jan. 30, 2002

(86) PCT No.: PCT/EP02/00956

§ 371 (c)(1),
(2), (4) Date: Feb. 3, 2004

(87) PCT Pub. No.: WO02/060932

PCT Pub. Date: Aug. 8, 2002

(65) Prior Publication Data

US 2004/0115773 A1   Jun. 17, 2004

(30) Foreign Application Priority Data

Jan. 30, 2001   (EP) .................................. 01102050

(51) Int. Cl.
*C12P 21/06*   (2006.01)

(52) U.S. Cl. ..................... 435/69.1; 536/23.1; 536/24.2; 536/24.32; 435/320.1; 435/71.1; 435/6; 435/243; 435/252.3

(58) Field of Classification Search ................ 536/23.1, 536/24.2, 24.32; 435/320.1, 69.1, 71.1, 6, 435/243, 252.3
See application file for complete search history.

(56) References Cited

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7.*
Bourget et al (FEMS Microbiol. Letters. 110(1): 1993, pp. 11-20; abstract only at this time).*
Irving et al. "Phylogeny of the Serpin Superfamily: Implications of Patterns of Amino Acid Conservation for Structure and Function," Genome Res. 2000. 10:1845-1864.*
Document No. XP-002203432—Sasaki et al. "*Similar to Serpin—Wheat*" dated Dec. 1, 2001—1 sheet.
Létoffé et al. article entitled "Characterization of a protein inhibitor of extracellular proteases produced by *Erwinia chrysanthemi*" *Molecular Microbiology* (1989) 3(1), pp. 79-86.
Maeda et al. article entitled "Pathogenic Mechanisms Induced by Microbial Proteases in Microbial Infections" *Biol. Chem. Hoppe-Seyler*, vol. 377, pp. 217-226, Apr. 1996.

* cited by examiner

*Primary Examiner*—Jennifer E Graser
(74) *Attorney, Agent, or Firm*—K&L Gates LLP

(57) ABSTRACT

A novel gene of Bifidobacteria and the polypeptides encoded thereby. In particular, a gene belonging to the Serpin superfamily and its use in the production of bacterial Serpins is provided. Also provided are vectors, host cells, and methods for producing bacterial Serpin polynucleotides and/or polypeptides.

12 Claims, No Drawings

SEQUENCE LISTING

<160> NUMBER OF SEQ ID NOS: 2

<210> SEQ ID NO 1
<211> LENGTH: 1398
<212> TYPE: DNA
<213> ORGANISM: Bifidobacterium longum

<400> SEQUENCE: 1

| | | | | | |
|---|---|---|---|---|---|
| atgagcgagc | aactgatgga | acagtaccgg | ttgcgcggac | aacgcaaatg | ccgtaacgct | 60 |
| tgtatcgccg | ccatcgtgac | agtagtgctt | gtccttgccg | tcgccggcgg | cgtatggtgg | 120 |
| acggccggcg | atggcagcgc | attggttcgc | aatatgttca | agccgaaggc | cacgcctgcc | 180 |
| acgcagccgg | tagtcaacag | caccgcaacc | ttcgcctacc | gcaccgcacc | ggaattcctg | 240 |
| gcgatggaag | ccggcgaccg | aggcaccggc | aatgtgaact | actctcctgc | ttcgatgtgg | 300 |
| atggcgttgg | ccatcgccgc | gcagggcgcc | aatggcacga | cccgctcgca | actgaacgaa | 360 |
| ctgctgggct | ccggttcgct | gaccgatagc | gactaccaat | cgctgctaag | ttcgatcaac | 420 |
| gggcaatatt | cggggcgaa  | atccgagatg | agcgccgcga | actcgctgtg | gattgatgac | 480 |
| gactactctc | ttgccagcga | ttaccaatcc | accgtcaaga | agatgttcga | ggccgaagtc | 540 |
| accacgttac | cgttcgacga | tcaggccgcc | gccaagatgt | ccgattggat | tgccaagcat | 600 |
| acgaatggtt | cgctcaagcc | gaagatcacg | ctgcgtgacc | gtgaagtcct | gtccatcatc | 660 |
| aacaccgtct | atgcggatgg | ccgctggaag | gatccgttcg | aagagcagtc | caccggcaac | 720 |
| ggcaccttcc | acggcgaagc | cggagatgct | caggtgccga | tgatgcacca | gaccttcagc | 780 |
| caaatggctt | acggacatga | tgagtacaac | acttggcagc | gggtggagat | tccgttcgac | 840 |
| aacggcggca | atctggccat | cgtgctgccg | gccgaagggc | atttcgacga | gttggccggc | 900 |
| gatgccgaga | agctcagttg | ggcgttcggt | acatgctcga | cggcatccct | tggcgagggc | 960 |
| gcaatgggtt | gcgccgcgga | cagtatgccc | ggctggggcg | tctccgtcaa | ctcggtcatg | 1020 |
| gtgaacgtca | cgctaccgcg | attcaccatc | gacagcatgt | tcgactcgga | agccaccatc | 1080 |
| aaggcattcg | aaaaactggg | ggtgaccgat | gcgttcagtg | caggcgacgc | cgacttcacc | 1140 |
| aagatgatcg | acaccggttc | gcacggcgag | aacctgtata | tcggctcgat | tctgcaaggc | 1200 |
| acgcgcatcg | aggtgaacga | agccggcgcc | aaggccatgt | ccttcaccaa | ggtcggcgca | 1260 |
| gactccgtta | gcgcgccggt | ggacaacgtc | gagttcacgg | tggatcgccc | atttctgtat | 1320 |
| tcgtacgtca | ccccggacgg | cataccatta | ttcatcggtg | cggtgcgcaa | cctcggcgga | 1380 |
| gtcggtggag | aaaactga | | | | | 1398 |

<210> SEQ ID NO 2
<211> LENGTH: 465
<212> TYPE: PRT
<213> ORGANISM: Bifidobacterium longum

<400> SEQUENCE: 2

Met Ser Glu Gln Leu Met Glu Gln Tyr Arg Leu Arg Gly Gln Arg Lys
1               5                   10                  15

Cys Arg Asn Ala Cys Ile Ala Ala Ile Val Thr Val Leu Val Leu
            20                  25                  30

Ala Val Ala Gly Gly Val Trp Trp Thr Ala Gly Asp Gly Ser Ala Leu
        35                  40                  45

Val Arg Asn Met Phe Lys Pro Lys Ala Thr Pro Ala Thr Gln Pro Val
    50                  55                  60

-continued

```
Val Asn Ser Thr Ala Thr Phe Ala Tyr Arg Thr Ala Pro Glu Phe Leu
 65                  70                  75                  80

Ala Met Glu Ala Gly Asp Arg Gly Thr Gly Asn Val Asn Tyr Ser Pro
                 85                  90                  95

Ala Ser Met Trp Met Ala Leu Ala Ile Ala Ala Gln Gly Ala Asn Gly
            100                 105                 110

Thr Thr Arg Ser Gln Leu Asn Glu Leu Leu Gly Ser Gly Ser Leu Thr
            115                 120                 125

Asp Ser Asp Tyr Gln Ser Leu Leu Ser Ser Ile Asn Gly Gln Tyr Ser
            130                 135                 140

Gly Ala Lys Ser Glu Met Ser Ala Ala Asn Ser Leu Trp Ile Asp Asp
145                 150                 155                 160

Asp Tyr Ser Leu Ala Ser Asp Tyr Gln Ser Thr Val Lys Lys Met Phe
                165                 170                 175

Glu Ala Glu Val Thr Thr Leu Pro Phe Asp Asp Gln Ala Ala Ala Lys
            180                 185                 190

Met Ser Asp Trp Ile Ala Lys His Thr Asn Gly Ser Leu Lys Pro Lys
            195                 200                 205

Ile Thr Leu Arg Asp Arg Glu Val Leu Ser Ile Ile Asn Thr Val Tyr
210                 215                 220

Ala Asp Gly Arg Trp Lys Asp Pro Phe Glu Glu Gln Ser Thr Gly Asn
225                 230                 235                 240

Gly Thr Phe His Gly Glu Ala Gly Asp Ala Gln Val Pro Met Met His
                245                 250                 255

Gln Thr Phe Ser Gln Met Ala Tyr Gly His Asp Glu Tyr Asn Thr Trp
            260                 265                 270

Gln Arg Val Glu Ile Pro Phe Asp Asn Gly Gly Asn Leu Ala Ile Val
            275                 280                 285

Leu Pro Ala Glu Gly His Phe Asp Glu Leu Ala Gly Asp Ala Glu Lys
290                 295                 300

Leu Ser Trp Ala Phe Gly Thr Cys Ser Thr Ala Ser Leu Gly Glu Gly
305                 310                 315                 320

Ala Met Gly Cys Ala Ala Asp Ser Met Pro Gly Trp Gly Val Ser Val
                325                 330                 335

Asn Ser Val Met Val Asn Val Thr Leu Pro Arg Phe Thr Ile Asp Ser
            340                 345                 350

Met Phe Asp Ser Glu Ala Thr Ile Lys Ala Phe Glu Lys Leu Gly Val
            355                 360                 365

Thr Asp Ala Phe Ser Ala Gly Asp Ala Asp Phe Thr Lys Met Ile Asp
            370                 375                 380

Thr Gly Ser His Gly Glu Asn Leu Tyr Ile Gly Ser Ile Leu Gln Gly
385                 390                 395                 400

Thr Arg Ile Glu Val Asn Glu Ala Gly Ala Lys Ala Met Ser Phe Thr
                405                 410                 415

Lys Val Gly Ala Asp Ser Val Ser Ala Pro Val Asp Asn Val Glu Phe
            420                 425                 430

Thr Val Asp Arg Pro Phe Leu Tyr Ser Tyr Val Thr Pro Asp Gly Ile
            435                 440                 445

Pro Leu Phe Ile Gly Ala Val Arg Asn Leu Gly Gly Val Gly Gly Glu
            450                 455                 460

Asn
465
```

SERPIN IN BIFIDOBACTERIA

BACKGROUND OF THE INVENTION

The present invention pertains to a novel gene of Bifidobacteria and to the polypeptides encoded thereby. In particular, the present invention pertains to a gene belonging to the Serpin superfamily and its use in the production of bacterial Serpins. Also provided are vectors, host cells, and methods for producing bacterial Serpin polynucleotides and/or polypeptides.

Lactic acid bacteria have been utilized for the preservation and preparation of food material for long time taking benefit of the low pH and the action of products generated during the fermentative activity thereof. In addition, Lactic acid bacteria are involved in the production of a variety of different food products, such as cheese or yogurt.

Quite recently lactic acid bacteria, in particular Lactobacilli and Bifidobacteria, have attracted a great deal of attention in that some strains have been found to exhibit valuable properties to man and animals upon ingestion. These strains, which are generically designated probiotics, have been found to be capable to survive the severe environmental conditions prevailing in the gastric tract and be able to at least transiently colonize the intestinal mucosa, where they bring about positive effects for the living beings having incorporated them.

In EP 0 768 375 such a probiotic strain of the genus *Bifidobacterium* is disclosed, which is capable to become implanted in the intestinal flora. This *Bifidobacterium* is reported to assist in the immuno-modulation of the host, being able to competitively exclude adhesion of pathogenic bacteria to intestinal cells, thus supporting the maintenance of the individual's health.

Further, in EP 0 577 903 reference is made to the use of a lactic acid bacteria having the ability of replacing *Heliobacter pylori*, the acknowledged cause for the development of ulcer.

Also, in WO 97/00078 a specific *lactobacillus* strain, termed *Lactobacillus* GG (ATCC 53103), is disclosed as such a probiotic. The microorganism may be employed for preventing or treating food induced hypersensitivity reactions.

SUMMARY OF THE INVENTION

In view of the valuable properties these probiotic strains may provide, there is a desire for obtaining more detailed information about the biology of these strains, especially about the interaction with the hosts, the phenomena of surviving different environmental conditions in the gut as well as about the capability to adhere to the intestine's mucosa. In particular the involvement thereof in the enhancement of the immune system and defense against pathogens is of high interest.

Consequently, a problem of the present invention is to provide data about bacterial strains that exhibit properties beneficial for man and/or animals and occasionally elucidate.

In the line of investigating the genome of the probiotic *Bifidobacterium* strain BL29 the present inventors have surprisingly found a gene that shows a moderate homology to genes belonging to the Serpin superfamily (SERine Protease Inhibitors). Genes for such type of genes have so far only been found in cells of higher organisms, such as humans and plants, but not in bacterial cells.

In consequence, the present invention provides for a nucleic acid as identified by SEQ ID. NO. 1 or parts or variants thereof coding for a functional polypeptide, which variants have a homology to the SEQ ID. No. 1 of about 75%, preferably 80%, more preferably 85%, even more preferably 90% even more preferred 95%.

According to an alternative embodiment the present invention also pertains to a polypeptide as identified by SEQ ID. NO. 2 or functional parts or variants thereof, which variants have a degree of homology to the said SEQ. ID. No. 2 of about 75%, preferably 80%, more preferably 85%, even more preferably 90% even more preferred 95%.

Additionally, the present invention relates to the use of the polypeptides for identification, characterization and purification of molecules as well as for the treatment or prevention of disease. Moreover, methods of detecting probiotic strains and producing microorganisms expressing serpin are provided. Further, novel food and pharmaceutical products are provided, as well as vectors, host cells, and methods of producing bacterial serpin polynucleotides and/or polypeptides.

Additional features and advantages of the present invention are described in, and will be apparent from, the following Detailed Description of the Invention and the figures.

DETAILED DESCRIPTION OF THE INVENTION

Serine proteinase inhibitors (Serpins) comprise a diverse group of proteins that form a super-family including more than 100 members. The majority of Serpins act as protease inhibitors and are involved in the regulation of several proteinase-activated physiological processes, important for the individual, such as blood clotting, complement mediated lysis, the immune response, glomerulonephritis, pain sensing, inflammation, pancreatitis, cancer, regulating fertilization, bacterial infection and viral maturation. Though the primary function of Serpins appears to be neutralizing serine proteinase activity, these polypeptides have also been found to play a role in extracellular matrix remodelling and cell migration.

Examples for Serpins include, a1-antitrypsin, antithrombin III, plasminogen activator inhibitor 1 (PAI-1) or plasminogen activator inhibitor 2.

The Serpins known so far have been the subject of intensive Research and they all seem to have a common characteristic loop, termed the reactive site loop (RSL), extending from the surface of the molecule containing the recognition sequence for the active site of the cognate serine protease. The specificity of each inhibitor is considered to be determined primarily by the identity of the amino acid that is immediately amino-terminal to the site of potential cleavage of the inhibitor by the serine protease. This amino acid, known as the Pi site residue, is considered to form an acyl bond with the serine in the active site of the serine protease.

The Serpins seem to act as "suicide inhibitors" forming a 1:1 stoichiometric complex with the target proteinase, thus blocking their activity. According to recent data it has been indicated that the inhibitor is cleaved in the reactive center and that the complex is most likely trapped as a covalent acyl-enzyme complex.

Since Serpins are involved in sophisticated biological processes such as modulating the immune system or inflammatory reactions or even remodelling the extracellular matrix of a higher living being their presence in procaryotes has not been expected. In fact, no Serpin has so far been reported to be derived from procaryotic cells.

The present inventors are therefore the first to have found that also some bacterial cells may contain Serpins. Without wishing to be bound by any theory it is presently assumed that the probiotic properties, such as modulation of the immune system or the known property of the Bifidobacterial strain, from which it has been derived, may at least in part be due to the presence of the present Serpin.

In the context of this application a nucleic acid according to the present invention shall designate a poly-nucleotide as identified by SEQ. ID. NO. 1 or parts or variants thereof, that yield a functional polypeptide. To this end, the nucleic acid shown in SEQ ID NO. 1 may be truncated at its ends to an extent, at which the resulting polypeptide still yields the biological function. Likewise, the nucleic acid may also be modified by deleting, adding or replacing one or more nucleotides, with the proviso that the resulting polypeptide still exerts its biological function.

Similarly, the same applies to the polypeptide described herein. The term polypeptide according to the present invention shall designate a polypeptide as identified by SEQ. ID. NO. 2 or parts or variants thereof, that are functional. Therefore, the polypeptide of SEQ. ID. NO. 2 may be truncated at its ends to an extent, at which the polypeptide still yields the biological function. Likewise, the polypeptide may also be modified by having one or more amino acids being deleted, added or replaced, with the proviso that the resulting polypeptide still exerts its biological function.

According to an embodiment, the above mentioned nucleic acid may be inserted in a suitable host cell and expressed therein. For this purpose, a nucleic acid according to the present invention may be inserted in a suitable vector, which allows propagation and/or expression in the desired host cell and inserted therein. The vector will contain a marker gene to enable a stable propagation.

Likewise, the nucleic acid according to the present invention may also be included into the genome of the host, using the phenomenon of homologous recombination or other techniques, allowing insertion of a nucleic acid only into the host's chromosome. Such a technique is e.g. described in EP 93 105 303.7, the contents thereof is incorporated herein by way of reference.

The nucleic acid according to the present invention may be put under the control of an endogeneous or exogeneous regulon, e.g. a promotor, depending on whether the gene product shall be over-expressed, i.e. for collecting and purifying the polypeptide, or expressed to a certain extent to be delivered to an individual via a carrier system, such as a micro-organism. The regulon, e.g. the promoter, is preferably regulatable and/ or inducible and will be operably linked with the coding molecule via any of the well-recognized and easily-practised methodologies for so doing.

These recombinant constructs are then introduced for expression into suitable host cells such as, e.g., *E. coli*, Lactobacilli, Streptococci or Bifidobacteria as a prokaryotic host cell or *Saccharomyces cerevisiae*, insect cells, CHO or COS cells as eukaryotic host cells and the transformed or transduced host cells are cultured under conditions which allow expression of the heterologous gene. It will be appreciated that the gene product of the present polynucleotide will be subject to glycosylation upon expression in an eucaryotic expression system.

According to another aspect the present invention also comprises recombinant micro-organisms containing at least a copy of the nucleic acid according to the present invention. The nucleic acid may be included in a micro-organism, that is used to deliver the target-substance to the individual. In this respect probiotic bacteria are suitable, since they are able to pass the gastric tract of an individual and get at least transiently implanted into the mucosa of a host. At this location it will exert its biological function as is seen in the present probiotic strain BL29, from which it was derived. Without wishing to be bound by any theory it is presently thought that the gene product of the present nucleic acid is involved in the anti-inflammatory activity displayed by the Bifidobacterial strain BL29. Likewise, any bacterial strain, already including a nucleic acid according to the present invention may be used as a host cell, into which additional copies of the target nucleic acid may be included.

The host cell will express the gene product of a nucleic acid according to the present invention. Therefore, the host cells may be utilized for the synthesis of a polypeptide according to the present invention on large scale.

A "host cell" according to the present invention may be obtained by recombinant means, in that a nucleic acid according to the present invention is inserted in a suitable cell. However, in order to increase the amount of Bifido-Serpin in the Bifidobacteria containing such sort of polypeptides, the Bifidobacteria itself may be subjected to common techniques of mutation of selection such that a strain having an increased amount of the corresponding gene product is obtained.

The isolation of the protein can be carried out according to known methods from the host cell or from the culture supernatant of the host cell. Such methods are described for example by Ausubel I., Frederick M., Current Protocols in Mol. Biol. (1992), John Wiley and Sons, New York. The polypeptide can be purified after recombinant production by affinity chromatography using known protein purification techniques, including immuno-precipitation, gel filtration, ion exchange chromatography, chromatofocussing, isoelectric focussing, selective precipitation, electrophoresis, or the like.

The invention further comprises a method for detecting a nucleic acid or a polypeptide according to the present invention, comprising incubating a sample, e.g. cell lysates or a reverse transcript of an RNA sample, with either a nucleic acid molecule according to the invention and determining hybridization under stringent conditions of said nucleic acid molecule to a target nucleic acid molecule for determination of presence of a nucleic acid molecule, or using antibodies, preferably monoclonal antibodies raised against the polypeptide according to the present invention. Also a quantitative detection of the gene may be performed by PCR techniques, preferably by the use of quantitative RT-PCR using, e.g., the LightCycler™ of Roche Diagnostics GmbH, DE.

Since the Serpin gene seems to be associated with probiotic activity of bacterial strains, the present nucleic acid and/or polynucleotide may likewise be utilized for searching for additional strains exhibiting probiotic activities.

To determine, whether a given bacterial strain may be apt, the approximate amount of hybridization of the nucleic acid with the target nucleic acid or nucleic acids of the bacterial strain is determined. The approximate amount of hybridization may easily be determined qualitatively by e.g. visual inspection upon detecting hybridization. For example, if a gel is used to resolve labelled nucleic acid which hybridizes to target nucleic acid in the sample, the resulting band can be inspected visually. Likewise, as with the use of antibodies FACS may be utilized for a quantitative measurement.

The nucleic acid or a polypeptide according to the present invention may be utilized for the identification, characterization and/or purification of molecules affecting biological process associated with the activity of serine proteases. Exemplary biological processes, in which serine proteases are involved comprise blood coagulation, fibrinolysis, immune reactions, complement activation, inflammatory responses extra-cellular matrix turnover, cell migration and prohormone activation, cancer metastasis.

Likewise, the nucleic acid or polypeptide according to the present invention may also be used for the development of molecules eventually suitable in the treatment and/or diagnosis of disease states, which involve the activity of serine proteases. Once the interaction of the present Serpin with the target proteases has been understood, agonists or antagonists to the proteases, but likewise agonists or antagonists to Serpins may be devised. As mentioned above, non-limiting examples for disease states considered by the present invention are improper blood coagulation, improper fibrinolysis, immune reactions, complement activation, inflammatory responses extra-cellular matrix turnover, cell migration and prohormone activation, cancer metastasis.

The use of various model systems or structural studies will enable the development of specific agonists and antagonists useful in regulating the function of the present Serpin and the proteases to which it binds. It may be envisaged that these can be peptides, mutated ligands, antibodies or other molecules able to interact with the present Serpin.

The nucleic acid according to the present invention may in general be utilized for the synthesis of the polypeptide for large scale production thereof, by expressing a nucleic acid according to the present invention or a vector containing such a nucleic acid in a suitable host under conditions suitable for the expression of the polypeptide and collecting and purifying the polypeptide.

By way of example, the following examples illustrate the invention without limiting it thereto.

Example 1

Isolation of the Serpin Gene

In the line of sequencing the genome of the *Bifidobacterium longum* strain BL29 by the method of directed sequencing after fluorescent automated sequencing of the inserts of clones and assembling of these sequences of nucleotide fragments (inserts) by means of software programmes, an open reading frame has been found. To achieve that, fragments of the genome were created, ligated into suitable vectors for amplification and propagation and the corresponding fragments have been sequenced. Overlaps and the final arrangement of the fragments, the nucleotide sequence thereof, were assessed by the aid of appropriate soft-wares.

Protein and/or nucleic acid sequence homologies have be evaluated using the following algorithms:

(1) BLASTP: Compares an amino acid query sequence against a protein sequence database (2) BLASTN: Compares a nucleotide query sequence against a nucleotide sequence database (3) BLASTX: Compares a nucleotide query sequence translated in all reading frames against a protein sequence database (4) TBLASTN: Compares a protein query sequence against a nucleotide sequence database dynamically translated in all reading frames A modest overall homology to the known murine Serpin a-2-antiplasmin of about 43% has been noted. Yet the present polypeptide shows a homology of about 63% with the reactive site loop (RSL) thereof.

Example 2

Cloning of the Bifidobacterial Serpin Gene and Isolation of the Polypeptide

The nucleic acid encoding the putative Bifidobacterial Serpin deleted from its signal peptide, was cloned into the *E. coli* expression vector pDEST 17 (Invitrogen Life Technologies) and the corresponding protein was produced as a 6-His tagged fusion protein in *E. coli* (Janknecht R et al. (1991): Proc. Natl. Acad. Sci. USA:88(20) pp 8972-8976) according to common techniques.

The 6-His tagged protein was purified to homogeneity by metal affinity chromatography on a nickel-nitrilotriacetic acid matrix (Ni-NTA from Quiagen) according to the instructions described in the QIA-Expressionist Handbook from Quiagen, and used for production of functional studies as well as for production of polyclonal antibodies in rabbits.

Example 3

Potential Anti-Inflammatory Activity of a Serpin-Like Protein, Expressed in BL29

The polypeptide as isolated in example 2 has been used in a haemolytic assay in vitro in order to determine its activity as a Serpin.

To this end, 50 ml of successive doubling dilution of human AB serum (Sigma) were mixed in a 96 microtiter well plate with 50 ml of a 1.7% sheep antibody-activated sheep erythrocyte suspension. To assess anti-haemolytic activity of the recombinant Serpin, 1 mg of the recombinant protein was added to each well and the mixture was incubated for 1 hr at 37° C. The plate was then centrifuged to pellet intact cells and cell debris and the supernatant was transferred to a new plate. Haemolytic activity was estimated by measuring haemoglobin release as absorbance at 450 nm.

*Bifidobacterium* Serpin activity was compared to human serpin a1-antitrypsin (5 mg/well). Distilled water was used as positive control to obtain 100% erythrocyte lysis and human inactivated AB serum as negative control (no lysis due to complement inactivation).

The results clearly indicate that recombinant Serpin from Bifidobacteria inhibited human red blood cell lysis to a similar extent as human a1-antitrypsin, a known serine-protease inhibitor.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An isolated nucleic acid sequence comprising, SEQ ID, NO. 1 or variants thereof coding for a polypeptide having serine protease inhibitor activity, which variants have a homology to the SEQ ID. NO. 1 of at least 95%.

2. A vector containing a nucleic acid according to claim 1.

3. A host cell containing one or more copies of a nucleic acid according to claim 1.

4. The host cell according to claim 3, wherein the polypeptide is expressed.

5. A host cell comprising a recombinant DNA molecule in a host that expresses a polypeptide comprising SEQ ID. NO. 2 or variants thereof having serine protease inhibitor activity, and that have a degree of homology to the said SEQ ID. NO. 2 of at least 95%.

6. A method of producing a polypeptide having serine protease inhibitor activity, comprising the steps of obtaining a cell comprising a recombinant DNA that encodes a serine protease inhibitor activity, having at least 95% sequence homology to SEQ ID NO: 1, and placing the cell under conditions such that the recombinant DNA produces the polypeptide and purifying the polypeptide.

7. A method for identifying a microbial strains containing a gene for a Serpin polypeptide comprising the steps of incubating a sample with a nucleic acid molecule comprising SEQ. ID. NO. 1 or variants thereof coding for a polypeptide having serine protease inhibitor activity, which variants have a homology to the SEQ. ID. NO. 1 of at least 95%, detecting hybridization to said nucleic acid to determine the presence of a Serpin polypeptide gene in the micro-organism.

8. A method for producing a micro-organism expressing a Serpin polypeptide encoded by a recombinant nucleic acid comprising SEQ ID. NO. 1 or variants thereof coding for a polypeptide having serine protease inhibitor activity, which variants have a homology to the SEQ ID. NO. 1 of at least 95% comprising the steps of transforming a micro-organism with the recombinant nucleic acid comprising SEQ ID. NO. 1 or variants thereof coding for a polypeptide having serine protease inhibitor activity and expressing the gene encoding the Serpin polypeptide.

9. A food or pharmaceutical product comprising a recombinant nucleic acid sequence comprising SEQ ID. NO. 1 or variants thereof coding for a polypeptide having serine protease inhibitor activity, which variants have a homology to SEQ ID. NO. 1 of at least 95%.

10. A method of producing a polypeptide containing an amino acid sequence comprising SEQ ID. NO. 2 or variants thereof having serine protease inhibitor activity, that have a degree of homology to SEQ ID. NO. 2 of at least 95%, comprising the steps of obtaining a cell comprising a recombinant DNA that encodes the polypeptide, and placing the cell under conditions such that the polypeptide is expressed.

11. A method for identifying a microbial strains containing a gene for a Serpin polypeptide comprising the steps of incubating a sample with a nucleic acid molecule that encodes a polypeptide having the amino acid sequence comprising SEQ ID. NO. 2 or variants thereof coding for a polypeptide having serine protease inhibitor activity, which variants have a homology to the SEQ ID. NO. 2 of at least 95%, detecting hybridization to said nucleic acid to determine the presence of a Serpin polypeptide gene in the micro-organism.

12. A food or pharmaceutical product comprising a recombinant nucleic acid polymer that encodes a polypeptide comprising SEQ ID. NO. 2 or variants thereof coding for a polypeptide having serine protease inhibitor activity, which variants have a homology to the SEQ ID. NO. 2 of at least 95%.

* * * * *